United States Patent [19]

Pétré et al.

[11] Patent Number: 4,508,902
[45] Date of Patent: Apr. 2, 1985

[54] PROCESS FOR THE PREPARATION OF 4-HYDROXYQUINOLINES

[75] Inventors: Dominique Pétré, Paris; Daniel Michelet, Tassin, both of France

[73] Assignee: Rhone-Poulenc Sante, Courbevoie, France

[21] Appl. No.: 504,954

[22] Filed: Jun. 16, 1983

[30] Foreign Application Priority Data

Jun. 17, 1982 [FR] France ................. 82 10615

[51] Int. Cl.³ ........................................... C07D 215/22
[52] U.S. Cl. .............................................. 546/153
[58] Field of Search ...................................... 546/153

[56] References Cited

U.S. PATENT DOCUMENTS 2,558,211 6/1951 Elderfield ..................... 546/153
4,412,076 10/1983 Baudouin et al. ............. 546/153

OTHER PUBLICATIONS

Johnson et al., J.A.C.S., 74, 4513(1952).

*Primary Examiner*—Mark L. Berch
*Assistant Examiner*—Cecilia Shen
*Attorney, Agent, or Firm*—Stevens, Davis, Miller & Mosher

[57] ABSTRACT

Process for the preparation of a 4-hydroxyquinoline of the formula:

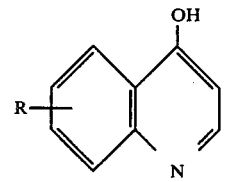

in which R represents a hydrogen atom or one, two or three substituents, which may be the same or different, selected from halogen atoms, alkyl radicals containing 1 to 4 carbon atoms, alkoxy radicals containing 1 to 4 carbon atoms, and the trifluoromethyl radical, the substituent(s) being in the 2-, 3-, 5-, 6-, 7- or 8-position, which comprises oxidizing a 1,2,3,4-tetrahydroquinolin-4-one of the general formula:

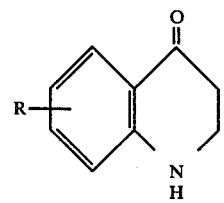

in which R is as hereinbefore defined, in a basic medium, under pressure, by means of excess oxygen or air at a temperature between 80° and 150° C.

The 4-hydroxyquinoline products are useful for the preparation of therapeutically useful substances.

6 Claims, No Drawings

PROCESS FOR THE PREPARATION OF 4-HYDROXYQUINOLINES

The present invention relates to a process for the preparation of 4-hydroxyquinolines of the general formula:

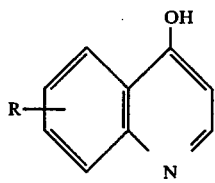
(I)

in which R represents a hydrogen atom or one, two or three substituents, which may be the same or different, selected from halogen atoms, alkyl radicals containing 1 to 4 carbon atoms, alkoxy radicals containing 1 to 4 carbon atoms, and the trifluoromethyl radical, the substituent(s) being in the 2-, 3-, 5-, 6-, 7- or 8-position, from the corresponding 1,2,3,4-tetrahydro-quinolin-4-ones of the general formula:

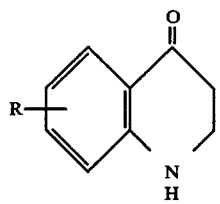
(II)

in which R is as hereinbefore defined.

The products of general formula (I) are particularly valuable intermediates for the synthesis of therapeutically active products such as glafenine [the dihydroxypropyl ester of N-(7-chloroquinol-4-yl)-anthranilic acid] or floctafenine [the dihydroxypropyl ester of N-(8-trifluoromethylquinol-4-yl)-anthranilic acid], which are powerful analgesics, or chloroquine [7-chloro-4-(4-diethylamino-1-methylbutylamino)-quinoline] or amodiaquin [7-chloro-4-(3-diethylaminomethyl-4-hydroxyphenylamino)-quinoline], which possess remarkable antimalarial properties.

It is known to prepare a 4-hydroxyquinoline from the corresponding quinolin-4-one either by catalytic dehydrogenation in the presence of palladium-on-charcoal [W. S. Johnson and B. G. Buell, J. Amer. Chem. Soc., 74, 4513 (1952)], or by hydrogen transfer catalysed by palladium-on-charcoal in the presence of maleic acid (U.S. Pat. No. 2,558,211). However, if a 1,2,3,4-tetrahydroquinolin-4-one of general formula (II) in which R represents a halogen atom is used, the aromatisation is accompanied by dehalogenation, which leads to the production of a mixture of halogenated 4-hydroxyquinoline and 4-hydroxyquinoline.

It has now been found that the 4-hydroxyquinolines of general formula (I) can be obtained by oxidation of the corresponding 1,2,3,4-tetrahydroquinolin-4-one in a basic medium, under pressure, by means of excess oxygen or air at a temperature between 80° and 150° C., it is this finding which forms the subject of the present invention.

The oxidation is carried out in a basic medium, preferably consisting of an aqueous solution of an alkali metal hydroxide such as sodium hydroxide. It is particularly advantageous to use from 0.5 to 3 mols of alkali metal hydroxide per mol of starting 1,2,3,4-tetrahydroquinolin-4-one. In general, an increase in the concentration of alkali metal hydroxide results in an increase in the reaction rate.

To enable the reaction to be carried out, it is necessary to operate under a pressure which is generally between 2 and 15 bars, the air or oxygen being injected at a suitable rate through the stirred reaction mixture. In general, an increase in pressure results in an increase in the reaction rate.

For reasons of convenience, it is particularly advantageous to carry out the reaction at a temperature between 90° and 100° C., under a pressure of between 5 and 10 bars and using from 1 to 2 mols of sodium hydroxide per mol of starting 1,2,3,4-tetrahydroquinolin-4-one. Under these conditions, the reaction is complete after a heating time of 2 to 6 hours.

Carrying out the process according to the invention on a halogeno-1,2,3,4-tetrahydroquinolin-4-one makes it possible to obtain the corresponding halogeno-4-hydroxyquinoline virtually free of 4-hydroxyquinoline.

The 4-hydroxyquinolines of general formula (I) obtained by the process of the present invention can be separated from the reaction mixture and purified by applying the usual methods such as crystallisation or chromatography.

The 1,2,3,4-tetrahydroquinolin-4-ones of general formula (II) used as starting material can advantageously be prepared by cyclisation of the corresponding 3-anilinopropionic acid by means of a mixture of hydrofluoric acid and boron trifluoride.

The 3-anilinopropionic acids can be obtained by reacting an excess of an appropriately substituted aniline with acrylic acid. The reaction is generally carried out in water at a temperature of between 70° and 100° C. The reaction time is between 1 and 4 hours.

By way of example, 7-chloro-4-hydroxyquinoline obtained in accordance with the process of the present invention can be converted to glafenine by the process described in French Pat. No. 2413 M, after conversion to 4,7-dichloroquinoline, e.g. by means of phosphorus oxychloride.

The following examples, which are given without implying a limitation, show how the invention can be put into practice:

EXAMPLE 1

The following are introduced into a 400 cc stainless steel autoclave fitted with a blade stirrer, a condenser, a gas inlet and a gas outlet:

| | |
|---|---|
| 7-chloro-1,2,3,4-tetrahydro-quinolin-4-one | 18.15 g (100 millimols) |
| sodium hydroxide | 8.0 g (200 millimols) |
| water | 200 g |

The reactor is heated to 90° C. The pressure is set at 10 bars. Air containing 21% of oxygen is injected in excess into the stirred reaction mixture at a rate of 12 g/hour.

After a heating time of 2 hours 30 minutes, the reactor is cooled to a temperature of about 20° C. and the pressure is brought back to atmospheric pressure.

The reaction mixture is extracted with methylene chloride. The methylene chloride phase is evaporated to dryness. A light yellow solid (0.96 g) is collected, which contains 98.2% (by weight) of 7-chloro-1,2,3,4-tetrahydroquinolin-4-one (5.2 millimols) as determined by liquid phase chromatography.

The aqueous phase is adjusted to pH 6.0 by adding N sulphuric acid. The milky white precipitate is filtered off and dried. A creamy white product (15.92 g) is collected, which contains 98.15% (by weight) of 4-hydroxy-7-chloroquinoline as determined by liquid phase chromatography, i.e. 87.0 millimols.

The filtrate is acidified to pH 2.5 by adding N sulphuric acid and is then extracted with methylene chloride. The methylene chloride phase is evaporated to dryness. A brown product (1.15 g) is collected. This product contains 4-hydroxy-7-chloroquinoline (0.59 g; 3.4 millimols) and 2-amino-4-chlorobenzoic acid (0.31 g; 1.8 millimols) as determined by liquid phase chromatography.

The proportion of the 5-chloroisomer is of the order of 0.7% as determined by gas chromatography.

EXAMPLES 2 TO 9

The procedure of Example 1 is followed using 7-chloro-1,2,3,4-tetrahydroquinolin-4-one (18.15 g; 100 millimols) as the starting material each time, and varying the reaction parameters. The results are collated in Table I, in which Q = 7-chloro-1,2,3,4-tetrahydroquinolin-4-one
OCQ = 4-hydroxy-7-chloroquinoline
OH/Q = molar ratio of the sodium hydroxide to the 7-chloro-1,2,3,4-tetrahydroquinolin-4-one
DC = degree of conversion of the 7-chloro-1,2,3,4-tetrahydroquinolin-4-one
Y = yield relative to the 7-chloro-1,2,3,4-tetrahydroquinolin-4-one converted.

TABLE I

| Example | Temp. (°C.) | Pressure (bars) | OH/Q | Time (hours) | Basic extract (Q) | Precipitate pH 6.0 (OCQ) | Extract pH 2.5 (OCQ) | DC % | Y % |
|---|---|---|---|---|---|---|---|---|---|
| 2 | 83 | 10 | 2 | 4¼ hrs. | 5.4 g (29.4 mM) | 11.7 g (61.9 mM) | 1.1 g (4.2 mM) | 70.5 | 94 |
| 3 | 110 | 10 | 2 | 2 hours | 0.4 g (1.6 mM) | 16.6 g (90 mM) | 1.1 g (3.4 mM) | 98.4 | 95.2 |
| 4 | 140 | 10 | 2 | 3 hours 20 mins. | 0.2 g (1.1 mM) | 14.3 g (73 mM) | 3.8 g (10 mM) | 98.9 | 84.2 |
| 5 | 90 | 2 | 2 | 6 hours 20 mins. | 7.4 g (40 mM) | 10.5 g (57.4 mM) | 1.2 g (2.6 mM) | 60 | 100 |
| 6 | 90 | 5 | 2 | 4½ hours | 1.3 g (6.4 mM) | 15.8 g (81.4 mM) | 1.0 g (3.2 mM) | 93.6 | 90.4 |
| 7 | 90 | 10 | 1.1 | 5¼ hours | 4.6 g (24.5 mM) | 12.2 g (65.2 mM) | 1.3 g (3.8 mM) | 75.5 | 91.4 |
| 8 | 90 | 10 | 0.5 | 2½ hours | 11.2 g (62 mM) | 6.2 g (34.1 mM) | 1.0 g (3.2 mM) | 38 | 98.1 |
| 9 | 90 | 10 | 0 | 5 hours | 18.1 g (100 mM) | — | — | 0 | 0 |

In this Table "mM" signifies millimols.

Chloride ions (2.9 millimols) are determined by silver titrimetry on the remaining aqueous phase.

The 4-hydroxy-7-chloroquinoline is obtained with a degree of conversion of 94.8% of the 7-chloro-1,2,3,4-tetrahydroquinolin-4-one, and a yield of 4-hydroxy-7-chloroquinoline of 95.3% relative to the 7-chloro-1,2,3,4-tetrahydroquinolin-4-one converted.

The starting 7-chloro-1,2,3,4-tetrahydroquinolin-4-one can be prepared in the following manner:

3-m-Chloroanilinopropionic acid (95.4% pure) (10 g) is introduced into a stainless steel reactor containing liquid hydrofluoric acid (50 g) cooled to 5° C. The solution is saturated with gaseous boron trifluoride. For this purpose, the contents of the reactor are kept at 20° C. and then saturated with gaseous boron trifluoride under a pressure of 12 bars for 1 hour. The reactor is then closed and heated at 80° C. for 20 hours.

During heating, the pressure rises initially to 20 bars and then falls gradually and stabilises at about 16 bars. The reactor is then cooled to 10° C. and opened so as to allow the boron trifluoride to escape. The reddish liquid obtained is poured into a mixture of water and ice. After extraction with chloroform (3×100 cc), the organic layer is washed several times with water (100 cc) to a pH of between 3 and 4 and then dried over sodium sulphate. After filtration and concentration to dryness under reduced pressure (10 mm Hg; 1.33 kPa), crystalline 7-chloro-1,2,3,4-tetrahydroquinolin-4-one (9 g) is obtained, which is 94.5% pure as determined by gas chromatography.

The degree of conversion is 100% and the yield relative to the 3-m-chloroanilinopropionic acid is 99%.

EXAMPLE 10

The following are introduced into a 150 cc autoclave (useful volume 80 cc) fitted with a "Rushton turbine" type stirrer (rotation speed 750 rpm), a condenser, a gas inlet and a gas outlet:

| | |
|---|---|
| 8-trifluoromethyl-1,2,3,4-tetrahydroquinolin-4-one | 2.705 g (12.58 millimols) |
| sodium hydroxide | 1 g (25 millimols) |
| water | 2.5 cc. |

The reactor is heated to 90° C. The pressure is set at 10 bars. Air containing 21% of oxygen is injected in excess into the stirred reaction mixture at a rate of about 5 liters/hour.

After a heating time of 7 hours, the reactor is cooled to a temperature of about 20° C. and the pressure is brought back to atmospheric pressure.

The reaction mixture is extracted with methylene chloride. By evaporation to dryness of the methylene chloride phase, unconverted starting material (1.913 g; 8.9 millimols) is obtained, which contains traces of 8-trifluoromethyl-4-hydroxyquinoline.

The aqueous phase is adjusted to pH 6.0 by adding N sulphuric acid, and is then extracted with normal butanol. The butanol is evaporated off under reduced pressure. Virtually pure 8-trifluoromethyl-4-hydroxyquinoline (0.616 g; 2.90 millimols) is thus collected.

The degree of conversion is 29.3% and the yield relative to the starting material converted is 78.5%.

The 8-trifluoromethyl-1,2,3,4-tetrahydroquinolin-4-one can be prepared in the following manner:

3-o-Trifluoromethylanilinopropionic acid (23.3 g) is introduced into a stainless steel reactor containing liquid hydrofluoric acid (100 g) cooled to 5° C. The solution is saturated with gaseous boron trifluoride. For this purpose, the contents of the reactor are kept at 20° C. and then saturated with gaseous boron trifluoride under a pressure of 17 bars for 1 hour. The reactor is then closed and heated at 80° C. for 19 hours.

After cooling to 10° C., the reactor is opened so as to allow the boron trifluoride to escape. The liquid obtained is poured into a mixture of water and ice. After extraction with chloroform, the organic layer is washed with water and then dried over sodium sulphate. After filtration and concentration under reduced pressure (10 mm Hg; 1.33 kPa), 8-trifluoromethyl-1,2,3,4-tetrahydroquinolin-4-one (13.9 g) is obtained, which is 99% pure as determined by gas chromatography.

The degree of conversion is 68.7% and the yield relative to the 3-o-trifluoromethylanilinopropionic acid converted is of the order of 95%.

EXAMPLE 11

The procedure of Example 10 is followed using

| 7-methyl-1,2,3,4-tetrahydro-quinolin-4-one | 1.636 g (10.16 millimols) |
|---|---|
| sodium hydroxide | 1 g (25 millimols) |
| water | 2.5 cc | as the starting materials.

The reaction mixture is heated for 14.5 hours under the conditions of Example 10 and is then treated in the same manner.

Starting material (0.215 g), which corresponds to a degree of conversion of 86.9%, and virtually pure 7-methyl-4-hydroxyquinoline (1.278 g; 8.04 millimols) are collected.

The yield relative to the starting material converted is 91%.

7-Methyl-1,2,3,4-tetrahydroquinolin-4-one can be prepared in the following manner:

3-m-Methylanilinopropionic acid (18.5 g) is introduced into a stainless steel reactor containing liquid hydrofluoric acid (100 g) cooled to 5° C. The solution is saturated with gaseous boron trifluoride. For this purpose, the contents of the reactor are kept at 20° C. and then saturated with gaseous boron trifluoride under a pressure of 11 bars for 1 hour. The reactor is then heated at 82° C. for 23 hours.

After cooling to 10° C., the reactor is opened so as to allow the boron trifluoride to escape. The liquid obtained is poured into a mixture of water and ice. After extraction with chloroform, the organic layer is washed with water and then dried over sodium sulphate. After filtration and concentration to dryness under reduced pressure (10 mm Hg; 1.33 kPa), 7-methyl-1,2,3,4-tetrahydroquinolin-4-one (16.6 g) is obtained, which is 96% pure as determined by gas chromatography.

The degree of conversion is of the order of 100% and the yield relative to the 3-m-methylanilinopropionic acid converted is of the order of 100%.

The proportion of the 5-methyl isomer is less than 1% as determined by gas chromatography and nuclear magnetic resonance.

EXAMPLE 12

The procedure of Example 10 is followed using

| 7-chloro-2-methyl-1,2,3,4-tetrahydroquinolin-4-one | 1.937 g (9.9 millimols) |
|---|---|
| sodium hydroxide | 1 g (25 millimols) |
| water | 2.5 cc | as the starting materials.

The reaction mixture is heated for 7.5 hours under the conditions of Example 10 and is then treated in the same manner.

Starting material (1.209 g), which corresponds to a degree of conversion of 37.6%, and virtually pure 7-chloro-2-methyl-4-hydroxyquinoline (0.692 g; 3.57 millimols) are collected.

The yield relative to the starting material converted is 96%.

7-Chloro-2-methyl-1,2,3,4-tetrahydroquinolin-4-one can be prepared in the following manner:

3-m-Chloroanilinobutanoic acid (21.4 g) is introduced into a stainless steel reactor containing liquid hydrofluoric acid (100 g) cooled to 5° C. The solution is saturated with gaseous boron trifluoride. For this purpose, the contents of the reactor are kept at 20° C. and then saturated with gaseous boron trifluoride under a pressure of 10 bars for 1 hour. The reactor is then closed and heated at 82° C. for 24 hours.

After cooling to 10° C., the reactor is opened so as to allow the boron trifluoride to escape. The liquid obtained is poured into a mixture of water and ice. After extraction with chloroform, the organic layer is washed with water and then dried over sodium sulphate. After filtration and concentration to dryness under reduced pressure (10 mm Hg; 1.33 kPa), 7-chloro-2-methyl-1,2,3,4-tetrahydroquinolin-4-one (18.3 g) is obtained, which is 95% pure as determined by gas chromatography.

The degree of conversion is 93.5% and the yield relative to the 3-m-chloroanilinobutanoic acid converted is of the order of 100%.

The proportion of the 5-chloro isomer is less than 1% as determined by gas chromatography and nuclear magnetic resonance.

We claim:

1. A process for the preparation of a 4-hydroxyquinoline of the formula:

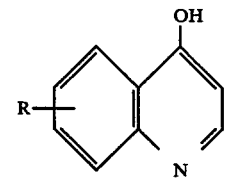

in which R represents a hydrogen atom or one, two or three substituents, which may be the same or different, selected from halogen atoms, alkyl radicals containing 1' to 4 carbon atoms, alkoxy radicals containing 1 to 4 carbon atoms, and the trifluoromethyl radical, the substituent(s) being in the 2-, 3-, 5-, 6-, 7- or 8-position, which comprises oxidising a 1,2,3,4-tetrahydroquinolin-4-one of the formula:

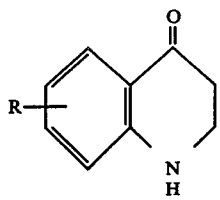

in which R is as hereinbefore defined, in a basic medium but in the absence of a catalyst, under pressure, by means of excess oxygen or air at a temperature between 80° and 150° C.

2. A process according to claim 1 in which the basic medium consists of an aqueous solution of an alkali metal hydroxide.

3. A process according to claim 2 in which the alkali metal hydroxide is sodium hydroxide.

4. A process according to claim 2 in which 0.5 to 3 mols of alkali metal hydroxide are used per mol of starting 1,2,3,4-tetrahydroquinolin-4-one.

5. A process according to any one of claims 1 to 4 in which the reaction is carried out under a pressure of 2 to 15 bars.

6. A process according to claim 1 or 2 in which the oxidation of the quinolin-4-one by means of excess oxygen or air is carried out at a temperature between 90° and 100° C. under a pressure of between 5 and 10 bars and using from 1 to 2 mols of sodium hydroxide per mol of starting 1,2,3,4-tetrahydroquinolin-4-one.

* * * * *